(12) United States Patent
Buccola et al.

(10) Patent No.: US 10,709,589 B2
(45) Date of Patent: Jul. 14, 2020

(54) ACCELERATED AGING FOR POLYMERIC SCAFFOLDS

(71) Applicant: Abbott Cardiovascular Systems Inc., Santa Clara, CA (US)

(72) Inventors: Jana Buccola, Rocklin, CA (US); Joel Harrington, Redwood City, CA (US); Syed Hossainy, Hayward, CA (US); Mary Beth Kossuth, San Jose, CA (US); Annie Liu, Cupertino, CA (US); James Oberhauser, Saratoga, CA (US); Fuh-Wei Tang, Temecula, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 246 days.

(21) Appl. No.: 15/590,817

(22) Filed: May 9, 2017

(65) Prior Publication Data

US 2018/0325707 A1 Nov. 15, 2018

(51) Int. Cl.
| | |
|---|---|
| *A61F 2/90* | (2013.01) |
| *A61F 2/91* | (2013.01) |
| *A61L 31/04* | (2006.01) |
| *A61L 31/14* | (2006.01) |
| *B29C 71/00* | (2006.01) |
| *A61F 2/82* | (2013.01) |
| *A61F 2/915* | (2013.01) |

(52) U.S. Cl.
CPC .................. *A61F 2/90* (2013.01); *A61F 2/91* (2013.01); *A61L 31/04* (2013.01); *A61L 31/041* (2013.01); *A61L 31/148* (2013.01); *B29C 71/0009* (2013.01); *A61F 2/82* (2013.01); *A61F 2/915* (2013.01); *A61F 2210/0004* (2013.01)

(58) Field of Classification Search
CPC .................. A61F 2/90; A61F 2240/001; A61F 2210/0004; A61F 2/82; A61L 31/148
USPC ......................................................... 73/865.6
See application file for complete search history.

(56) References Cited

U.S. PATENT DOCUMENTS

| | | |
|---|---|---|
| 2007/0050018 A1 | 3/2007 | Wainwright et al. |
| 2011/0146385 A1* | 6/2011 | Weinberg ................. G01N 3/36 73/37 |

(Continued)

OTHER PUBLICATIONS

"Non-Clinical Engineering Tests and Recommended Labeling for Intravascular Stents and Associated Delivery Systems" Apr. 18, 2010. U.S. Department of Health and Human Services Food and Drug Administration Center for Devices and Radiological Health. fda.gov, accessed Jun. 7, 2019. (Year: 2010).*

(Continued)

*Primary Examiner* — Nimeshkumar D Patel
*Assistant Examiner* — Jean F Morello
(74) *Attorney, Agent, or Firm* — Squire Patton Boggs (US) LLP

(57) ABSTRACT

A method of accelerated aging of bioresorbable polymer scaffolds including exposing the scaffold to water is disclosed. The scaffold is exposed to water at a controlled temperature for a selected aging time. The functional outputs, such as radial strength, expandability, and % recoil obtained from aged scaffolds predict those of real-time aging of the scaffold. The accelerated aging factor, which is the required shelf life divided by the aging time, is significantly higher for poly(L-lactide) scaffolds tested than thermal aging.

4 Claims, 14 Drawing Sheets

(56) References Cited

U.S. PATENT DOCUMENTS

| | | |
|---|---|---|
| 2012/0042501 A1 | 2/2012 | Wang et al. |
| 2014/0025161 A1* | 1/2014 | Stankus ................ A61L 31/148 623/1.19 |
| 2014/0114398 A1* | 4/2014 | Hossainy ................ A61L 31/06 623/1.16 |
| 2016/0081824 A1 | 3/2016 | Harrington et al. |
| 2016/0081827 A1 | 3/2016 | Lumauig et al. |

OTHER PUBLICATIONS

International Search Report and Written Opinion dated Aug. 3, 2018, for PCT Application No. PCT/US2018/028925, 14 pages.
T W Duerig et al. "An Overview of Superelastic Stent Design", Min. Invas. Ther. & Allied Technologies, 2000: 9(3/4): 235-246.
International Preliminary Report on Patentability dated Nov. 21, 2019 for PCT Application No. PCT/US2018/028925, 11 pages.

\* cited by examiner

ACCELERATED AGING FOR POLYMERIC SCAFFOLDS

BACKGROUND OF THE INVENTION

Field of the Invention

This invention relates accelerated aging of polymeric medical devices, in particular, bioresorbable stents or scaffolds.

Description of the State of the Art

This invention relates to accelerated aging of radially expandable endoprostheses that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts.

Most current stents are metallic and are permanent implants. This invention relates primarily to stent or scaffolds that are made partially or completely of polymers, in particular, polymers whose in vivo lifetime is finite. Such temporary stents are often referred to as bioresorbable scaffolds. Such scaffolds are intended to be bioresorbable, bioerodible, bioabsorbable, or biodegradable.

Stents and scaffolds are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of a scaffold or scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty.

Like most implantable medical devices, stents or scaffold are manufactured and then stored for a period of time until implanted. During a storage period a medical device undergoes aging which refers generally to changes in the device, such as physical, chemical, mechanical, or structural changes which may adversely impact the performance of the device. The aging may result in changes to certain functional outputs of the device that are important for its performance. These functional outputs may have specifications set by manufacturers and regulatory agencies. The functional outputs may be required to remain above or below a minimum or maximum specification, respectively, during a desired or an approved shelf life.

Shelf life refers to a time interval that a finished product is expected to remain within the approved shelf life specification during storage, provided that it is stored under the conditions defined on the container label. A finished product may refer to a packaged and sterilized device that contains all the materials (e.g. drug, polymers and other excipients) applied to or incorporated within the device and the delivery system in the final immediate packaging intended for marketing.

The shelf life of many medical devices, including stents and scaffolds, is in the range of months and years. Determining reliable estimates of shelf life of medical devices as rapidly as possible is a crucial aspect of product development. Rather than real-time aging, accelerated aging is often used to determine shelf life of medical devices. Accelerated aging is testing that uses aggravated or exaggerated conditions, for example, heat, to speed up the normal aging processes of product. It is used to help determine the long-term effects of expected levels of stress within a shorter time, usually in a laboratory by controlled standard test methods. It is used to estimate the useful lifespan of a product or its shelf life when actual lifespan data is unavailable.

Functional outputs of bioresorbable scaffolds relating to mechanical properties of the material include radial strength, expandability, and recoil. It is essential that they remain within product specifications during a designated shelf life. Therefore, reliable and fast accelerated aging methods are needed to speed up product development and facilitate regulatory approval.

INCORPORATION BY REFERENCE

All publications, patents, and patent applications mentioned in this specification are herein incorporated by reference to the same extent as if each individual publication, patent, or patent application was specifically and individually indicated to be incorporated by reference, and as if each said individual publication, patent, or patent application was fully set forth, including any figures, herein.

SUMMARY OF THE INVENTION

Embodiments of the invention include a method of accelerated aging of a bioresorbable polymeric scaffold comprising: providing a bioresorbable polymeric scaffold having a structure composed of a network of interconnecting struts, wherein scaffold is in a crimped configuration; exposing the scaffold to water at a controlled temperature for a selected aging time less than a desired shelf life of the scaffold, wherein a functional output of the scaffold changes during the exposing; and after the selected aging time, measuring the functional output of the scaffold using an appropriate standard test method.

The embodiments may include one or any combination of the following:
  selecting the aging time and the controlled temperature so that the measured functional output is within 10% of a measured functional output of the scaffold from real time aging for a time 100 to 1000 times greater than the aging time; wherein the aging time and the controlled temperature are such that the measured functional output is within 10% of a measured functional output of the scaffold from real time aging for a time 100 to 1000 times greater than the aging time; wherein the measured functional output is within 10% of a measured functional output of the scaffold subjected to real time aging for a shelf life; wherein a temperature of the water is 30 to 45° C.; wherein a temperature of the water is 10 to 45° below a glass transition temperature of the bioresorbable polymer of the scaffold; wherein the functional output is radial strength which is decreased by the accelerated aging; wherein the functional output is expandability which is decreased by the accelerated aging; wherein the functional output is recoil post-deployment; wherein the measured functional output is within 10% of a measured functional output of the scaffold subjected to real time aging for a shelf life 100 to 1000 times greater than the aging time; wherein the temperature is selected so that the functional output at the aging time is within 10% of the functional output of the scaffold after real time aging for a shelf life; wherein the network of interconnecting struts includes regions that deform when the scaffold is crimped which causes deformation induced damage to the scaffold in the region; wherein the scaffold is exposed to water without radially constraining the scaffold that would prevent outward recoil during the exposing; wherein the scaffold is exposed to water with a perforated sheath disposed over the scaffold that allows exposure to an outer surface of the scaffold and reduces or prevents outward recoil during the exposing; and prior to exposing the scaffold to water, aging the scaffold in a gas at ambient temperature for 1 to 30 days, wherein the radially constraining the scaffold which would prevent outward recoil.

Embodiments of the invention include a method of accelerated aging of a bioresorbable polymeric scaffold comprising: providing a bioresorbable polymeric scaffold in a crimped configuration and a sheath disposed over the scaffold for radial restraint; thermally aging the scaffold in a gas for a first aging time at a first aging temperature between 30 and 55° C.; removing the sheath from the scaffold; aging the scaffold in water after removal of the sheath at a second temperature between 25 and 40° C. for a second aging time, wherein a functional output of the scaffold changes during the thermal aging and the water aging; and determining the functional output of the water and thermally aged scaffold.

The embodiments may include one or both of the following: wherein an accelerated aging factor (AAF) is 6 to 10 for the thermal aging and the AAF is 100 to 1000 for the aging in water; and wherein the first aging time is 1 to 30 days and wherein the second aging time is 12 to 36 hours; Embodiments of the invention include a method of accelerated aging of a bioresorbable polymeric scaffold comprising: providing a bioresorbable polymeric scaffold comprising poly(L-lactide); aging the scaffold under conditions selected to provide an accelerated aging factor of 100 to 1000 for a functional output of the polymer scaffold; and determining a functional output after the aging, wherein a functional output is selected from the group consisting of radial strength, expandability, and % Recoil.

The embodiments may include the conditions comprise exposure to water at a controlled temperature in a range of 25 and 40° C.

Embodiments of the invention include a method comprising: providing a first bioresorbable polymeric scaffold made of a material comprising poly(L-lactide), wherein the scaffold is characterized by a set of scaffold parameters; perform accelerated aging of the scaffold in water under conditions that provide an accelerated aging factor of 100 to 1000 for predicting a functional output of the scaffold for a period of real-time storage; if the predicted functional output is less than a minimum specification or greater than a maximum specification for the functional output, providing a second bioresorbable polymeric scaffold made of the material, wherein the scaffold is characterized by the same set of scaffold parameters with at least one modified to improve the functional output; and performing the accelerated aging in water under the same conditions for the second scaffold.

The embodiments may include the scaffold structure includes a network of interconnected struts including undulating rings with crests and the scaffold parameters include number of crests, angles at crests, lengths of struts between crests, thickness of struts, and ratio of thickness to width of struts.

DETAILED DESCRIPTION OF THE INVENTION

Figure 1:
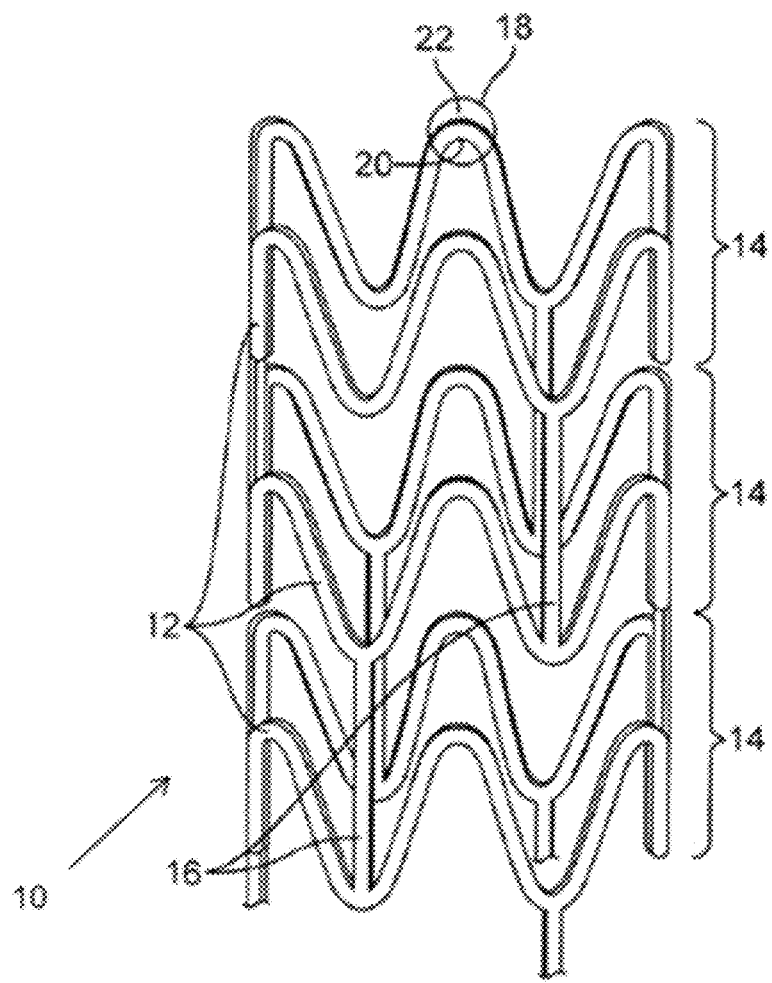
FIG. 1 depicts an exemplary scaffold.

The aging of products or materials refers to the variation of their properties over time, the properties of interest being those related to safety and efficacy of the product. Accelerated aging can be defined as a procedure that seeks to determine the response of a device or material under normal-usage conditions over a relatively long time, by subjecting the product for a much shorter time to exaggerated conditions that include stresses that are more severe or more frequently applied than normal environmental or operational stresses. The measured properties of a device during one or more time points of an accelerated aging process with exaggerated conditions may correspond to measured properties at longer time points of a real-time aging process of a device under normal storage conditions.

One reason for using accelerated aging techniques in the qualification testing of an implantable medical device is to bring the product to market at the earliest possible time.

The present invention relates to accelerated aging of bioresorbable polymer scaffolds that includes exposing the polymer scaffold to water for an aging time at a controlled temperature. The accelerated aging speeds up changes to the scaffold that occurs during real time storage of a Finished Goods (FG) scaffold. Functional outputs, such as radial strength, expandability, and recoil at deployment, measured at the end of an aging time correspond to functional outputs measured from real time aging. Real-time aging corresponds to aging the scaffold under real-life storage conditions, e.g., sterilized and package at ambient temperature. The real-time aging time is significantly longer than the accelerated aging time, for example, 100 to 1000 times larger, which dramatically speeds up product development.

A radially expandable stent or scaffold can have virtually any structural pattern that is compatible with a bodily lumen in which it is implanted. In certain aspects, a stent is composed of a pattern or network of circumferential rings and longitudinally extending interconnecting structural elements of struts or bar arms. The struts are arranged in patterns, which are designed to contact the lumen walls of a vessel and to maintain vascular patency.

A stent or scaffold can be made partially or completely from a biodegradable, bioresorbable, bioabsorbable, or biostable polymer. A polymer for use in fabricating a stent or scaffold can be biostable, bioresorbable, bioabsorbable, biodegradable or bioerodable. Biostable refers to polymers that are not biodegradable. The terms biodegradable, bioresorbable, bioabsorbable, and bioerodable are used interchangeably and refer to polymers that are capable of being completely degraded and/or eroded into different degrees of molecular levels when exposed to bodily fluids such as blood and can be gradually resorbed, absorbed, and/or eliminated by the body. The processes of breaking down and absorption of the polymer can be caused by, for example, hydrolysis and metabolic processes.

A stent made from a biodegradable polymer is intended to remain in the body for a period of time until its intended function of, for example, maintaining vascular patency and/or drug delivery is accomplished. After the process of degradation, erosion, absorption, and/or resorption has been completed, no portion of the biodegradable stent, or a biodegradable portion of the stent will remain. In some embodiments, very negligible traces or residue may be left behind.

Amorphous or semi-crystalline polymers that are stiff or rigid under biological conditions or conditions within a human body are particularly suitable for use as a scaffolding material. Specifically, polymers that have a glass transition temperature (Tg) sufficiently above human body temperature which is approximately 37° C., should be rigid upon implantation. Poly(L-lactide) (PLLA) is an example of such a polymer.

Exemplary bioresorbable polymers for a stent or scaffold include polylactide-based polymers such as, but are not limited to poly(L-lactide) (PLLA), poly(D,L-lactide), poly (L-lactide-co-caprolactone) (PLLA-co-CL), poly(L-lactide-co-glycolide) (PLGA), or poly(DL-lactide-co-glycolide). The copolymers may be random or block copolymers. The poly(DL-lactide) homopolymer or copolymer component of a polymer formulation can have a constitutional unit weight percentage L-lactide and D-lactide units of 50/50 to 96/4, such as 50/50 or 96/4 poly(DL-lactide). The term "unit" or "constitutional unit" refers to the composition of a monomer as it appears in a polymer.

The bioresorbable polymer may further be a blend of PLLA and poly(L-lactide-co-caprolactone) copolymer, referred to as PLLA/PCL where the percentage of PLLA and PCL, PLLA/PCL: 95/5, 90/10, 97/3; 96.2/3.8, and/or 99/1. For the PLLA/PCL blend, the PLLA may be 80 to 95 wt % of the blend and the copolymer may be 5 to 20 wt % of the blend.

An exemplary structure of a stent body or scaffold is shown in FIG. 1. FIG. 1 depicts a stent 10 which is made up of struts 12. Stent 10 has interconnected cylindrical rings 14 composed of undulating struts. Cylindrical rings 14 are connected by linking struts or links 16. The rings include crests 18 having an inner side 20 and an outer side 22. When the scaffold is crimped to a reduced delivery configuration, the crests 18 bend inward to allow a reduction in diameter. Similarly, when the scaffold is expanded to a deployed configuration in a vessel, the crests 18 bend outward to allow an increase in diameter. During crimping and deployment, the crest region is subjected to deformation. Specifically, inner side 20 experiences compressive deformation and the outer side 22 tensile deformation and the reverse for deployment.

The embodiments disclosed herein are not limited to stents or to the stent pattern illustrated in FIG. 1. The embodiments are easily applicable to other stent patterns and other devices. The variations in the structure of patterns are virtually unlimited. The outer diameter of a fabricated stent (prior to crimping and deployment) may be between 0.2-5.0 mm. For coronary applications, a fabricated stent diameter is 2.25-5 mm. The length of the stents may be between about 6-38 mm or more depending on the application.

Stents may also provide biological therapy. Biological therapy uses medicated stents to locally administer a therapeutic substance. A medicated stent may be fabricated by coating the surface of the polymeric scaffold with a polymeric carrier that includes an active or bioactive agent or drug. Polymeric scaffolds may also serve as a carrier of an active agent or drug. An active agent or drug may also be included on a scaffold without being incorporated into a polymeric carrier.

A polymer coating on the surface of a stent body or scaffold may also include a biodegradable polymer. The biodegradable polymer may be a carrier for an active agent or drug. The coating polymer may be bioresorbable.

A radial thickness or thickness of the stent body or scaffold may be 80 to 100 microns, 90 to 110 microns, 100 to 120 microns, 120 to 140 microns, 140 to 160 microns, or greater than 160 microns.

A biodegradable stent may be fabricated from a tube with a thin wall initially having no holes or voids. The pattern of structural elements may be formed by cutting out sections of the wall, for example, by laser machining. The sections that are removed results in the pattern of structural elements.

The diameter of an as-cut or laser cut scaffold for coronary applications may be 2.5 to 4.5 mm or more narrowly, 3 mm, 3.5 mm, 4.25, 4.5, or 2.8 to 4.25 mm.

The manufacturing process for a bioresorbable stent may include several steps. A polymeric tube may be formed using melt processing such as extrusion or injection molding. Prior to laser machining, the tube may be processed to modify its mechanical properties that also improve stent properties such as radial strength and resistance to fracture. Such processes may include radially deforming the tube. The scaffold pattern may then be formed by laser machining. A therapeutic coating may be formed over the scaffold.

Scaffolds and stents traditionally fall into two general categories: balloon expanded and self-expanding. In either case, the scaffold or stent is mounted over a delivery system in a reduced diameter or delivery configuration which allows the stent or scaffold to be inserted and transported through a blood vessel. The latter type expands (at least partially) to a deployed or expanded state within a vessel when a radial restraint is removed, while the former relies on an externally-applied force to configure it from a crimped or stowed state to the deployed or expanded state. The outer diameter of a crimped scaffold may be 0.049 to 0.065 in, or more narrowly, 0.053 to 0.057 in, 0.055 in, 0.054 to 0.056 in, or 0.061 to 0.065 in.

In the case of a balloon expandable stent, the scaffold is mounted about a balloon portion of a balloon catheter. The balloon has a labeled nominal expansion diameter. The scaffold is compressed or crimped onto the balloon. Crimping may be achieved by use of an iris-type or other form of crimper, such as the crimping machine disclosed and illustrated in US 2012/0042501. A significant amount of plastic or inelastic deformation, for example in the crest region of the scaffold, occurs both when the balloon expandable stent or scaffold is crimped and later deployed by a balloon. At the treatment site within the lumen, the stent is expanded by inflating the balloon to the nominal diameter. The scaffold may also be post-dilated by the balloon to greater than the nominal diameter.

Prior to packaging, a hollow removable sheath maybe disposed over the scaffold to reduce or prevent outward recoil of the scaffold during storage. The sheath is removed at the time of an implantation procedure.

A crimped scaffold is typically packaged in a sealed container in an inert gas or a mixture of an inert gas and oxygen. The packaged scaffold may then be sterilized using radiation, such as E-beam radiation. A scaffold crimped over a delivery system in a sealed package and sterilized is referred to as being a finished goods or a finished goods (FG) scaffold.

The performance of a bioresorbable polymer scaffold may be characterized by several functional outputs relating to mechanical properties. These include radial strength, expandability or expansion capability, and recoil post-deployment. For a given treatment application, these functional outputs each have specifications. The radial strength and the expandability have minimum specifications while the recoil has a maximum specification.

A scaffold is designed so that its functional outputs are maintained above a minimum specification or below a maximum specification, respectively, at least up until the desired or designated shelf life of the scaffold. It has been observed that these functional outputs change for bioresorbable polymer scaffolds during typical storage conditions for a scaffold. The scaffolds are stored in a crimped configuration in the sealed package in an inert gas or a mixture of an inert gas and oxygen. The storage temperature may be at or below 25° C., 20 to 30° C., or 15 to 25° C.

With respect to radial strength, stents or scaffolds are generally made to withstand the structural loads, namely radial compressive forces, imposed on the stent as it supports the walls of a vessel. Therefore, a stent must possess adequate radial strength if its function is to support a vessel at an increased diameter. Radial strength, which is the ability of a stent to resist radial compressive forces, relates to a stent's radial yield strength and radial stiffness around a circumferential direction of the stent.

A stent's "radial yield strength" or "radial strength" (for purposes of this application) may be understood as the compressive loading or pressure, which if exceeded, creates a yield stress condition resulting in the stent diameter not returning to its unloaded diameter, i.e., there is irrecoverable deformation of the stent. See, T. W. Duerig et al., Min Invas Ther & Allied Technol 2000: 9(3/4) 235-246. When the radial yield strength is exceeded, the stent is expected to yield more severely and only a minimal force is required to cause major deformation. Radial strength is measured either by applying a compressive load to a stent between flat plates or by applying an inwardly-directed radial load to the stent. The radial strength of the scaffold may be measured by expanding the scaffold from the crimped state to a deployed state in water, saline, simulated body fluid, or bodily fluid at or about 37° C.

The radial strength specification of a scaffold depends on a treatment application. For example, for coronary applications, the specification may be may be at least 300, 350 mm Hg, 300 to 400 mm Hg, 400 to 500 mm Hg, 500 to 650, 650 to 800 mm Hg, or 800 to 1100 mm Hg.

The maximum expansion capability or expandability of a scaffold refers generally to the ability to a scaffold to be expanded from a crimped state (e.g., in saline or bodily fluid) to a deployed state without failure and/or with the capability to provide a clinical useful radial strength. The degree may be quantified by the maximum diameter that the scaffold may be deformed or expanded without fracture or the diameter at which the scaffold fractures. The expansion capability may be inferred from a maximum expansion diameter, typically, inside diameter (ID), value. The maximum ID may be derived from a ring tension test or a post-dilation-to-fracture (PDtF) test. For coronary applications, the maximum ID may be 3.2 to 5 mm, or more narrowly, 2.75, 3.0, 3.25, 3.5 mm, 4.25 mm, 4.5 mm, 5 mm, 3.2 to 3.8 mm, 3.3 to 3.7 mm, or 3.5 to 4.25 mm. The maximum ID may be selected to be a certain amount above a nominal expansion diameter, for example, 0.5 mm above the nominal expansion diameter.

A "Ring test" (or "Ring Tension test") evaluates the capacity of a scaffold to sustain tension forces up until a point of total failure in one or more struts, typically a ring strut. The Ring Test is described in US 2016/0081827. An alternative test for measuring the fitness of a scaffold ring is called a post-dilation-to-fracture test. This test directly measures a maximum expanded diameter of a scaffold up until failure using balloons. According to the post-dilation-to-fracture test a scaffold is expanded on progressively larger balloons while watching for the first fracture, usually of a ring. The recorded test output for the post-dilation-to-fracture test is then the expanded inner-diameter of the rings just prior to the first ring fracture.

"Recoil" refers generally to the response of a material following the plastic/inelastic deformation of the material. Thus, when a scaffold is radially expanded by applied balloon pressure and the balloon removed, the scaffold will tend to return towards the smaller diameter it had, i.e., crimped diameter, before balloon pressure was applied. The % Recoil may be measure at the nominal deployment diameter or a larger post-dilated deployment diameter. The percent recoil (% Recoil) is calculated as $$\% \text{ Recoil}=100\%\times[\text{Deployed diameter}-\text{Recoil diameter}]/\text{Deployed diameter}.$$

Unless stated otherwise, when reference is made to "recoil" it is meant to mean recoil along a radial direction. The recoil effect for balloon-expanded scaffolds can increase with time after deployment, so is time dependent. "Acute Recoil" is defined as the percentage decrease in scaffold diameter within the first about ½ hour following implantation within a vessel. The maximum specification of % Recoil may be 8 to 10%, or more narrowly, 10%.

It was found during the development of bioresorbable scaffolds that the critical functional outputs relating to mechanical performance, including radial strength, maximum expansion capability, and recoil post-deployment, are a function of storage time and depend on structure-property changes during storage conditions.

The structure-property changes during storage can be simplified to be the result of two primary contributors at a molecular level, which are physical aging and stress relaxation. They lead to a third phenomenon of deformation-induced damage, where the microstructural changes from physical aging and stress relaxation affect the magnitude of damage to the material which results from the actions of both crimping and deploying the scaffold. The changes in functional performance over time are demonstrated to be proportional to the extent of chain rearrangement as characterized by changes in Tg.

The physical aging process is a volumetric shrinkage, or densification, of amorphous materials held below their glass transition temperature, Tg. Quenching a polymer at a finite rate of cooling to a temperature at or below its glass transition temperature and below freezes the long range molecular motion (>20 mer) and allows for only short range molecular motion (1-10 mer). This finite rate of cooling therefore prevents the polymer chains from reaching their equilibrium state, resulting in excess free volume. The short range mobility of the molecules with excess free volume within the glassy state leads to local chain rearrangement, allowing the system to densify and become less ductile. This results in an increase of excess enthalpy and increase in glass transition temperature over time as measured during heating of the polymer. The rate of physical aging depends on the amount of amorphous material available, the extent of the excess free volume, and the aging temperature relative to the Tg of the polymer.

The increase in excess enthalpy and glass transition temperature should result in an increase in both the modulus and the yield strength of a polymer. It has been observed for laser-cut PLLA scaffolds (i.e., scaffolds that have not been crimped) either before or after e-beam sterilization that radial strength increases with elapsed time. This is consistent with the effects of densification.

In contrast, it has been observed that a FG scaffold (scaffold that hasbeen crimped, and then deployed to at least the nominal product diameter) exhibits a decrease in radial strength over the same time frame when measured the same way. This indicates that while the expected molecular-level changes are occurring in the PLLA, the impact of changes are not reflected when performing functional mechanical tests on deployed scaffolds. It is the increase in deformation-induced damage during deployment due to the molecular-level changes resulting from physical aging that causes the decrease in radial strength. Therefore, the observed aging behavior in finished goods is not driven simply by physical aging of the PLLA.

With regard to stress relaxation, all polymeric materials, including both amorphous polymers and semi-crystalline polymers, exhibit some stress relaxation response as a result of the material's viscoelastic nature. During the crimping process, the scaffold is subjected to a large strain which is essentially held constant by the application of a constraining sheath. The stress imposed during this process will relax over time as the chains rearrange themselves to accommodate the crimped state. Stress relaxation within the scaffold is initially very fast, decaying rapidly over the first hour, and then the material achieves a constant relaxation time for elapsed times up to 6 months at the allowed storage temperature of 25° C. This time frame is inconsistent with the time frame of functional output aging, and therefore this phenomenon is not believed to be the most significant.

Deformation-induced damage has been observed after deployment of the bioresorbable scaffolds on the inner edge of crests. The mechanics of the crimping process leads to localized regions of high compressive stress in the inner edge and high tensile stresses on the outer edges, which are reversed upon deployment of the device. It is in these regions of high tensile stress after deployment in the inner edges of the crests where damage appears. It is believed the extent of damage is likely tied to the amount of physical aging. It is also believed also that as the rate of physical aging slows, the damage is expected to stabilize.

The accelerated aging method typically used in industry for physical aging of polymeric medical devices entails holding the test article at a temperature higher than its standard storage temperature. The industry standard for modeling such aging is a derivative of the Arrhenius equation. The calculations are based on the assumption that the chemical reactions in the aging process of a material follow the Arrhennius reaction rate function. For example, when the rate of reaction, $Q_{10}$, is equal to 2, a 10° C. increase in temperature will cause the reaction rate to double.

This value of $Q_{10}$ is used along with input values of the recommended storage temperature, TRT, desired accelerated aging temperature, TAA, both in ° C., and the required shelf life in days. It is recommended that in order to avoid non-linear changes in the rate of reaction, the accelerated aging temperature is below the glass transition temperature by at least 10 degrees. From the rate of reaction and the recommended storage and desired accelerated aging temperatures, the accelerated aging factor, AAF is calculated using the formula:

$$AAF = Q_{10}^{[(TAA-TRT)/10]}$$

The accelerated aging factor is then used to calculate the accelerated aging period using the formula:

$$AAT = \text{required shelf life}/AAF$$

For example, with ambient temperature considered to be 25° C., storing a product for six months at 35° C. will result in a one-year accelerated aging. Similarly, storing a product at 45° C. for three months will result in an accelerated aging period of one year, and so on.

Observations of real-time aging behavior from the bioresorbable scaffolds (Abbott Absorb BVS scaffold from Abbott Vascular Inc., Santa Clara, Calif.) have shown that certain functional outputs grow closer to their specifications over time, in particular, % recoil (increases), radial strength (decreases), and expansion capability (PDtF or ring tension) (decreases). The two major contributors to the change in functional testing as a function of product age are identified as physical aging and deformation-induced damage (the interaction of the crimp and deployment deformation with physical aging), with minor contributions from stress relaxation. These changes can be modeled as an exponential decay and approach an asymptotic value by the shelf life. Those outputs most strongly influenced by physical aging and damage have a half-life that mirrors the changes in enthalpy seen during physical aging and measured using DSC (radial strength and expansion capability), whereas the output of % Recoil has a much longer half-life of decay.

Investigations were made using heat alone as the condition for accelerated aging of bioresorbable scaffolds. The accelerated aging data for those functional outputs did not appear to be representative of real-time aging. If the conformational changes achieved through application of heat were the same as those achieved through real-time aging, the functional output vs. time curves for accelerated aging and real-time aging would be expected to converge. Instead, applying heat resulted in significantly worse values for the three outputs and was believed to be non-representative.

Therefore, use of the industry standard $Q_{10}$ aging factor was shown to not capture changes in these functional outputs that were representative of real-time aging. In the absence of an alternative accelerated aging method, studies of bioresorbable polymer scaffolds such as Absorb have to be done using real-time aging. This significantly limits the speed with which new products can be commercialized.

The inventors considered water exposure as an exaggerated condition for accelerated aging. Exposure to water allows for local chain rearrangement within the amorphous regions of the semicrystalline polymer scaffold backbone to a more enthalpically favorable state. This rearrangement is very similar to what takes place during physical aging. Based on observations made on the effect of water exposure on deployed scaffolds in in vitro degradation studies, it is believed that exposing a scaffold to water in the crimped state would lead to conformational changes within the scaffold backbone that would closely mimic the changes that occur during real-time aging. By tailoring the temperature and soak time, conformational changes may be driven to a state comparable to that achieved during the scaffold shelf life. The inventors have performed studies to determine whether there was an appropriate soak condition that would produce data that were comparable to real-time aged data.

It is believed that water behaves like a plasticizer and increases the chain mobility of the molecules in the amorphous region immediately when submerging the bioresorbable samples in water. The plasticization effect increases the chain mobility (fluidity) of polymeric materials in the amorphous region and hence decreases the Tg. It has been observed that the water sorption of PLLA scaffolds reaches near equilibrium in approximately 60 minutes. The PLLA reaches approximately 50% of its final hydration value (0.3% water uptake) within two minutes.

It has been observed from studies that absorbed water increases the radial strength of an as-cut PLLA scaffold prepared and tested using the standard test method for circumferential radial strength. The radial strength has a sustained plateau reached after approximately one hour of water exposure. It is believed that the increase in the observed radial strength is due to the increase of segmental mobility leading to local chain rearrangements and small changes in % crystallinity.

The mechanism by which the water increases the chain mobility and causes structural rearrangement also has been investigated. Two hypotheses were proposed: (1) water enables efficient packing (densification), (2) water plasticizes lower molecular weight amorphous chains and/or chain ends, allowing them to crystallize at or near crystallite interfaces. It is believed that densification of the amorphous phase of PLLA is the primary mechanism responsible for the modulus increase for PLLA samples after exposure to water. The studies also show that the water enables efficient packing, thus enhancing specificity and magnitude of intermolecular interactions between water and PLLA and therefore its modulus. The significant increase in segmental mobility for hydrated PLLA samples causes this change in physical property almost instantaneously.

The small increase in crystallinity observed after hydration may also modify the mechanical properties. Such an increase in the degree of crystallinity could also contribute towards increase in the radial strength, although the impact is expected to be small.

The William-Landel-Ferry (WLF) Doolittle equation predicts that the time required to achieve a given polymer characteristic will be shorter on a logarithmic scale for high T-Tg values, where T is the aging temperature and Tg is the glass transition temperature of the aged polymer. Therefore, achieving a physical condition comparable to that at shelf life can be accomplished faster by increasing the value of T-Tg. Thus, T-Tg is directly proportional to the accelerated aging factor (AAF).

The T-Tg may be increased by increasing the aging temperature, decreasing the Tg, or both. Since water molecules act as plasticizers after sorption into the PLLA, exposure to water depresses the Tg. Therefore, the drop of Tg due to water plasticization will accelerate the chain rearrangement or physical aging of the bioresorbable polymer of the scaffold.

The inventors conclude that chain rearrangement due to plasticization suggests that the increase of Tg and modulus (embrittlement) by water is similar to physical aging via temperature, but at a much faster rate. In general, thermal physical aging can take months or years, whereas comparable aging using water may be accomplished in hours or days. For example, an AAF for thermal aging may be 6 to 10, such as 8, while the inventors have observed remarkably high AAF's for water aging which may be 100 to 1000.

Embodiments of a method of accelerated aging of a bioresorbable polymeric scaffold in water include providing a bioresorbable polymeric scaffold in a crimped configuration. The scaffold is exposed to water at a controlled temperature for a selected aging time that is less than a desired shelf life of the scaffold. A functional output of the scaffold changes during the exposing. After the selected aging time, the scaffold is subjected to a standard test method for the functional output to be measured.

The water exposure accelerates the change in the functional output that would occur under normal storage conditions. For example, the water aging may result in a decrease in radial strength as a function of accelerated aging time, a decrease in the maximum expansion ID, and an increase in % recoil.

The exposure to water may be performed by soaking the crimped scaffold in a water bath at a controlled temperature which may be higher than ambient temperature. The temperature may be controlled by disposing the water bath container on a heated surface or by disposing a heating element in the water. The water bath container may alternatively be disposed in an oven. The heated surface, heating element, or oven temperature are adjusted to control the temperature of the water bath to within a selected tolerance of the controlled temperature, such as within 0.5, 0.1, or 0.01° C.

In some embodiments, the water is not removed from the scaffold after the water exposure and before measuring a functional output. However, water can optionally be removed prior to functional output measurement. For example, the scaffold after exposure may be dried by blowing warm on the scaffold or baking the scaffold in an oven.

The aging time and the controlled temperature time are or may be selected such that the measured functional output from accelerated aging (AA) is at or about a measured functional output of the scaffold from real-time aging (RTA). The accelerated aging factor (AAF) may be 100 to 1000, or more narrowly, 100 to 300, 300 to 600, 600 so 700, 700 to 800, or 800 to 1000. The controlled temperature may be adjusted so that 24 hours of aging corresponds to the shelf life. The shelf life may be 12 months, 18 months, 24 months, 36 months, 12 to 24 months, 24 to 36 months, or 36 to 48 months.

The AA functional output may be within a specified tolerance of the RTA functional output. The specified tolerance may be 10%, 5%, 2%, or 1%.

The aging time may correspond to a selected point of real-time aging, such as desired shelf life. The aging temperature may be selected so that the functional output is within a specified tolerance of the RTA functional output.

The controlled temperature may be 30 to 50° C., or more narrowly about 30° C., about 35° C., 30 to 35° C., 35 to 40° C., or 45 to 50° C.

The Tg of the scaffold polymer may be greater than the controlled temperature (Tc). The difference between Tg and Tc may be 10 to 50° C., or more narrowly, about 20° C., about 25° C., about 30° C., 20 to 30° C., or 40 to 50° C. It has been observed that the AAF is directly proportional to the difference between Tg and T. Therefore, in order to maintain a certain AAF used for one polymer, when aging a polymer with a lower Tg, a lower Tc should be selected.

When a polymer scaffold is crimped to a reduced diameter and experiences plastic deformation, the scaffold may exhibit some outward recoil if not radially constrained. The outward recoil is time-dependent like the inward recoil post-deployment. In order to reduce or prevent such outward recoil during storage, a hollow sheath maybe disposed over the scaffold after crimping over a support. The scaffold with the sheath is then packaged, sterilized, and stored. The sheath typically covers all or most of the outside surface of the scaffold since the sheath may not have gaps between the inner and outer walls of the sheath.

It may be advantageous to perform the accelerated aging with water without a sheath with no radial constraint to allow exposure of the water to the outer surface to facilitate absorption of water in the scaffold. Thus, the sheath is removed from the scaffold prior to exposure to water. Since a scaffold is stored with the radial constraint of the sheath, accelerated aging in this way may not accurately capture the kinetics of stress relaxation. Accelerated aging without a sheath may result in a worst-case property value for those outputs influenced by stress relaxation such as % Recoil.

Alternatively, the scaffold may be aged in water with a perforated sheath placed over the scaffold for radial constraint. The perforated sheath may have a plurality of holes all the way through its wall. The holes allow exposure of water to the surface of the scaffold which facilitates absorption of water.

An embodiment of a method of accelerated aging may include a period of real-time aging of a scaffold followed by accelerated water aging. The method allows stress relaxation to occur in real-time, following by water exposure after sheath removal and placement in a water bath. Therefore, the method may result in a more accurate prediction of real-time aging recoil. The real-time aging may be performed in the packaged state or after removal from the package. The real-time aging period may be 30 min to 1 hr, 1 hr to 12 hr, 12 hr to 24 hr, 12 to 36 hr, or 24 hr to 1 month.

An embodiment of accelerated aging method may include a step of thermal aging of a packaged scaffold or unpackaged scaffold in air with a sheath followed by accelerated water aging. The thermal aging accelerates the rate of stress relaxation of the scaffold while still sheathed, prior to the water aging. The thermal aging temperature may be between 30° C. to 55° C. for a PLLA or PLLA-based scaffold. More narrowly, the thermal aging temperature may be 30° C., 35° C., 30° C. to 40° C., or 30° C. to 55° C. The thermal aging time may be 30 min to 1 hr, 1 hr to 12 hr, 12 hr to 24 hr, 12 to 36 hr, or 24 hr to 1 month.

An exemplary embodiment may include providing a bioresorbable polymeric scaffold in a crimped configuration and a sheath disposed over the scaffold for radial restraint. The scaffold may be thermally aged in a gas for a first aging time at a first aging temperature between 30 and 55° C. The gas may be the gas in a package or air. The sheath maybe removed from the scaffold and then aged at a second temperature between 25 and 40° C. for a second aging time. A functional output of the scaffold changes during the thermal aging and the water aging. A functional output of the water and thermally aged scaffold is then determined. The accelerated aging factor (AAF) may be 6 to 10 for the thermal aging and the AAF may be 100 to 1000 for the aging in water. The first aging time may be 1 to 30 days and the second aging time is12 to 36 hours.

Evaluating the water aging for a bioresorbable scaffold can include water aging a set of scaffolds for a set of aging times for a selecting aging temperature. The scaffolds are made of a selected bioresorbable polymer.

The scaffolds are then deployed and tested for one or more functional outputs. The procedure may be repeated for different aging temperatures. The aging data curve of functional output as a function of time may then be compared to real-time data for the functional output. The accelerated aging data for each functional output for the various temperatures is overlaid on a real-time aging curve to determine the accuracy of the accelerated aging in predicting the functional output. The accuracy for each aging temperature is assessed based convergence of the curve for one or more data points. Ideally, the accelerated aging data converges at least at and close to the shelf life. An accelerated aging factor can be determined for each temperature based on corresponding time points.

The aging parameters (aging temperature and accelerated aging factor) may be used to predict real-time aging functional outs of modified scaffolds made of the same material. Modifications may be made to the scaffold for the purpose of improving the functional outputs at various real time points, such as shelf life. For example, the scaffold may be modified to increase the radial strength, increase the maximum ID from post-dilate to fracture, or decreasing acute recoil. The modifications may result in a functional output meeting a specification or extending further beyond a specification.

Modifications may include modifying the scaffold pattern parameters such as number of crests, angles at crests, or lengths of struts between crests. Modifications may further include additives in the bioresorbable material such as radiopaque materials or bioceramic materials. Modifications may also include changing thickness and width of struts.

An exemplary embodiment of using accelerated water aging in modifying a scaffold to meet product specification may include performing accelerated aging of the scaffold in water under conditions that provide an accelerated aging factor of 100 to 1000 for predicting a functional output of the scaffold for a period of real-time storage. The scaffold is characterized by a set of scaffold parameters. If the predicted functional output is less than a minimum specification or greater than a maximum specification for the functional output, a second bioresorbable polymeric scaffold made of the material is aged under the same conditions. The second scaffold is characterized by the same set of scaffold parameters with at least one modified to improve the functional output.

The inventors performed water-accelerated aging studies on the Absorb scaffold. Real-time aging data was available to evaluate the results of the accelerated aging. The studies were used to evaluate the aging performance of some functional outputs, such as radial strength and expandability, which are known to have an impact due to physical aging. The studies also included evaluation of the water accelerated aging effect on Tg. The purpose was to demonstrate that (1) the Tg increases and (2) the drop in functional outputs due to chain rearrangement can be accelerated more rapidly by water.

Figure 2:
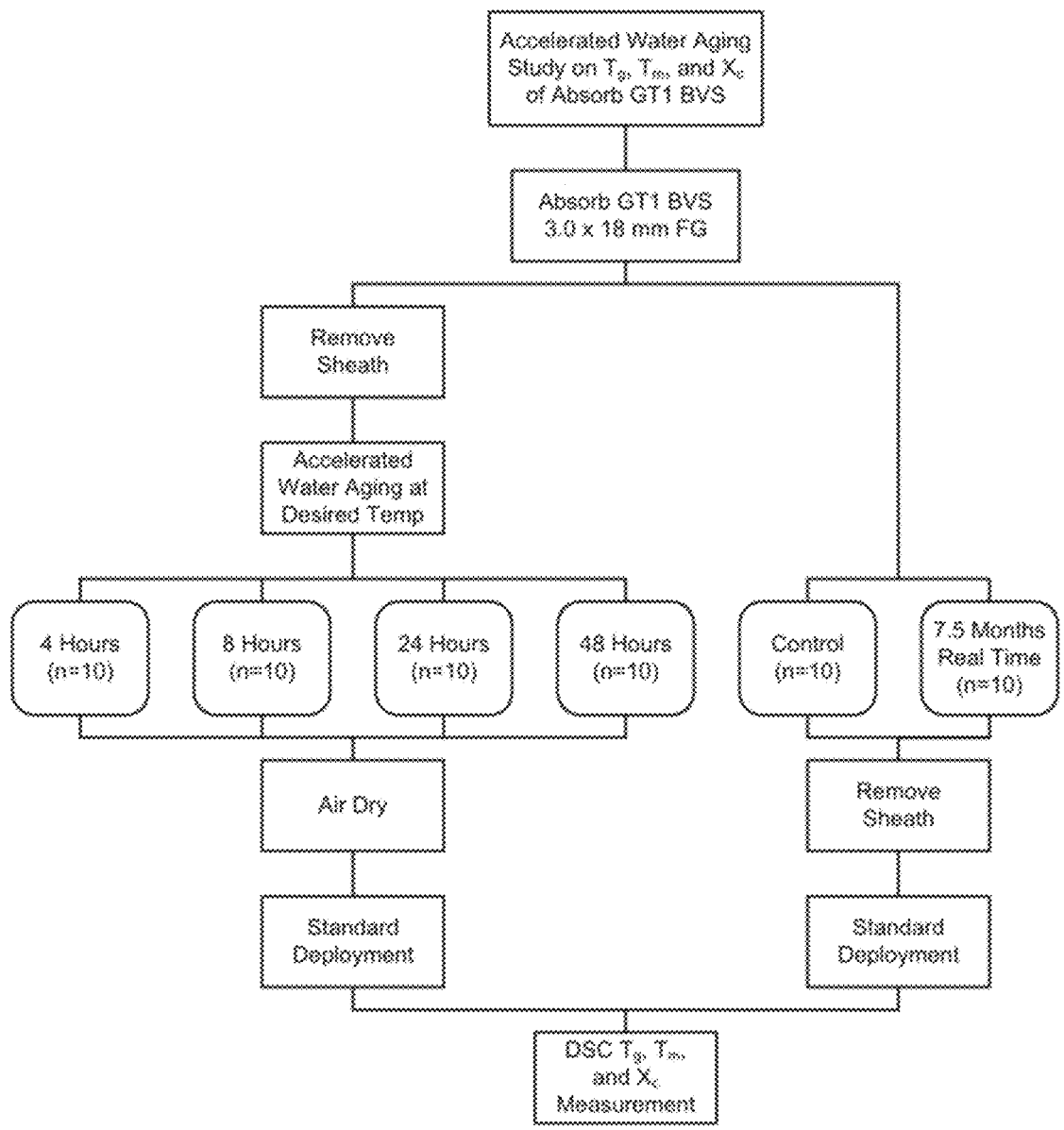
FIG. 2 depicts a study to evaluate the water accelerated aging effect on Tg of a scaffold.
Figure 3:
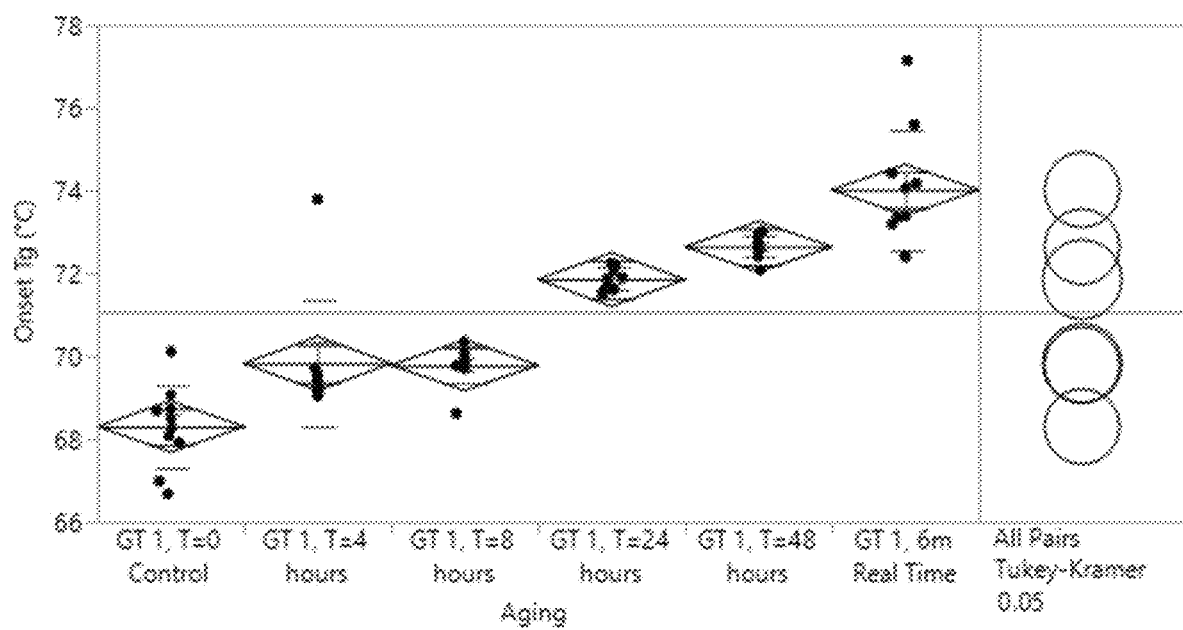
FIG. 3 depicts the water accelerated aging effect on Tg of the Absorb scaffold.

FIG. 2 depicts the study designed to evaluate the water accelerated aging effect on Tg of a scaffold. Test results are summarized in Table 1 and FIG. 3. The Tg was determined by dynamic mechanical analysis and the reported value is the onset Tg. It is observed that Tg increases as a function of water aging time for Absorb at a temperature higher than room temperature. The Tg increase does not quite reach the equivalent value for six months of real-time aging even after 48 hours of soak time. However, the trend is consistent with the observation for Tg increase in the real time aging and thermally accelerated aging studies.

TABLE 1

Water Accelerated Aging Effect on Glass Transition Temperature (Tg) of Absorb.

| | Absorb GT1 BVS | |
|---|---|---|
| Time Point | $T_g$ (° C.) | Stdev (° C.) |
| Control (0 hrs) | 68.31 | 0.99 |
| 4 hours | 69.83 | 1.50 |
| 8 hours | 69.79 | 0.45 |
| 24 hours | 71.85 | 0.28 |
| 48 hours | 72.65 | 0.26 |
| 6 months real time (no water) | 74.02 | 1.45 |

The scaffold functional attributes of radial strength, expansion capability, and % Recoil as a function of water-accelerated aging time for Absorb were also evaluated. A total of five functional outputs were evaluated: radial strength at nominal deployment, radial strength at post-dilated deployment, post-dilate to fracture (PDtF), % Recoil at nominal deployment, and % Recoil at post-dilated deployment.

Figure 4:
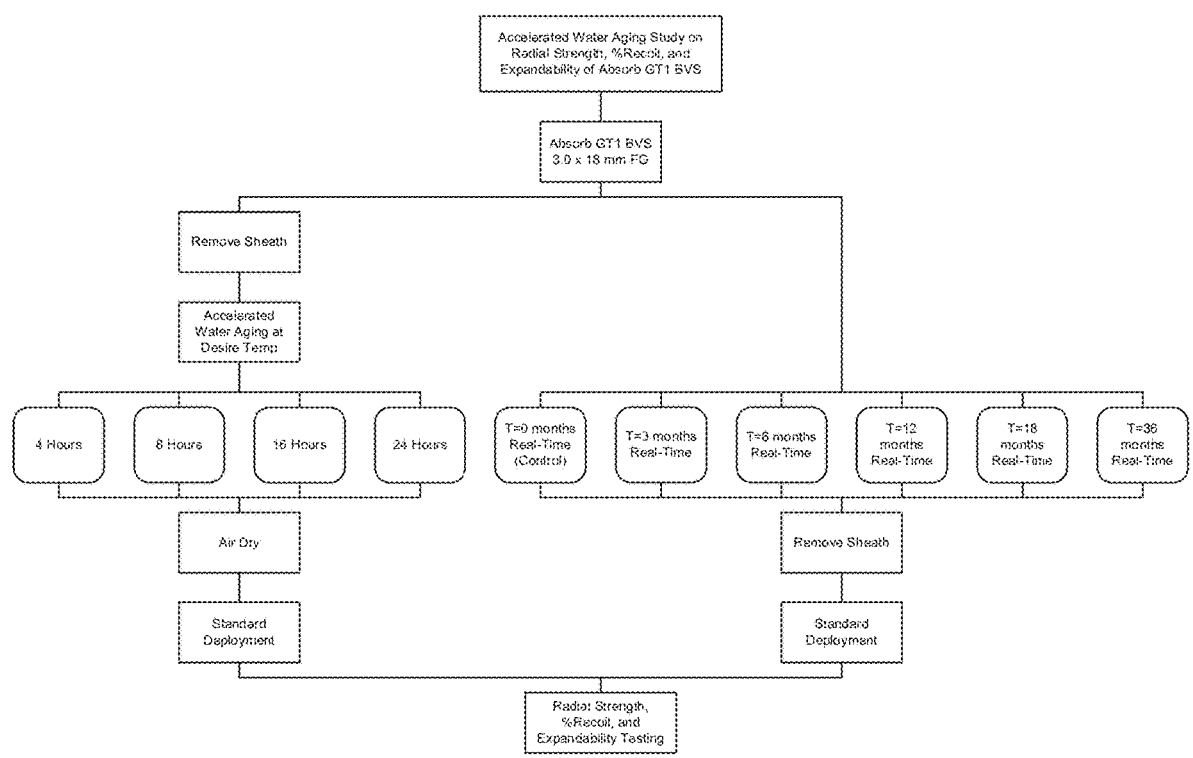
FIG. 4 depicts a study design for evaluating the scaffold functional attributes of radial strength, expansion capability, and % Recoil as a function of water-accelerated aging of a scaffold.

FIG. 4 depicts a study design for evaluating the scaffold functional attributes of radial strength, expansion capability, and % Recoil as a function of water-accelerated aging of a scaffold. Representative test results for Absorb mounted over a 3.0 mm nominal balloon size are summarized in Tables 2-6 and FIGS. 5-14.

Figure 5:
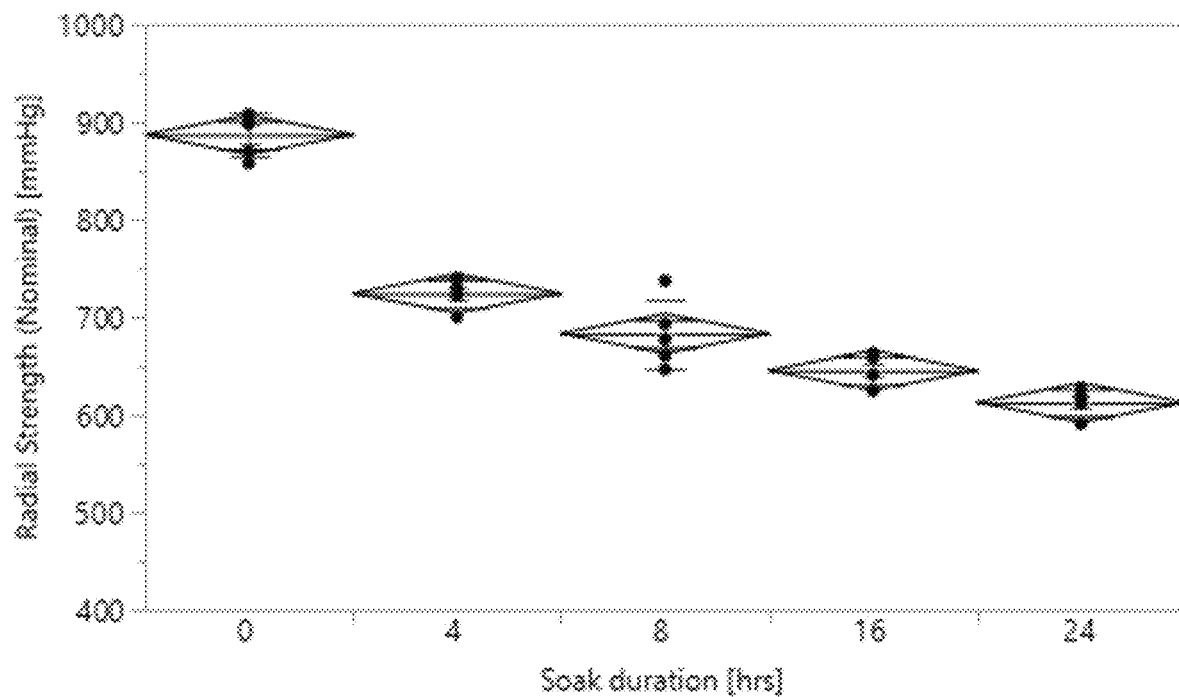
FIG. 5 depicts results for nominal radial strength of 3.0 mm diameter Absorb as a function of hours of water exposure time.
Figure 6:
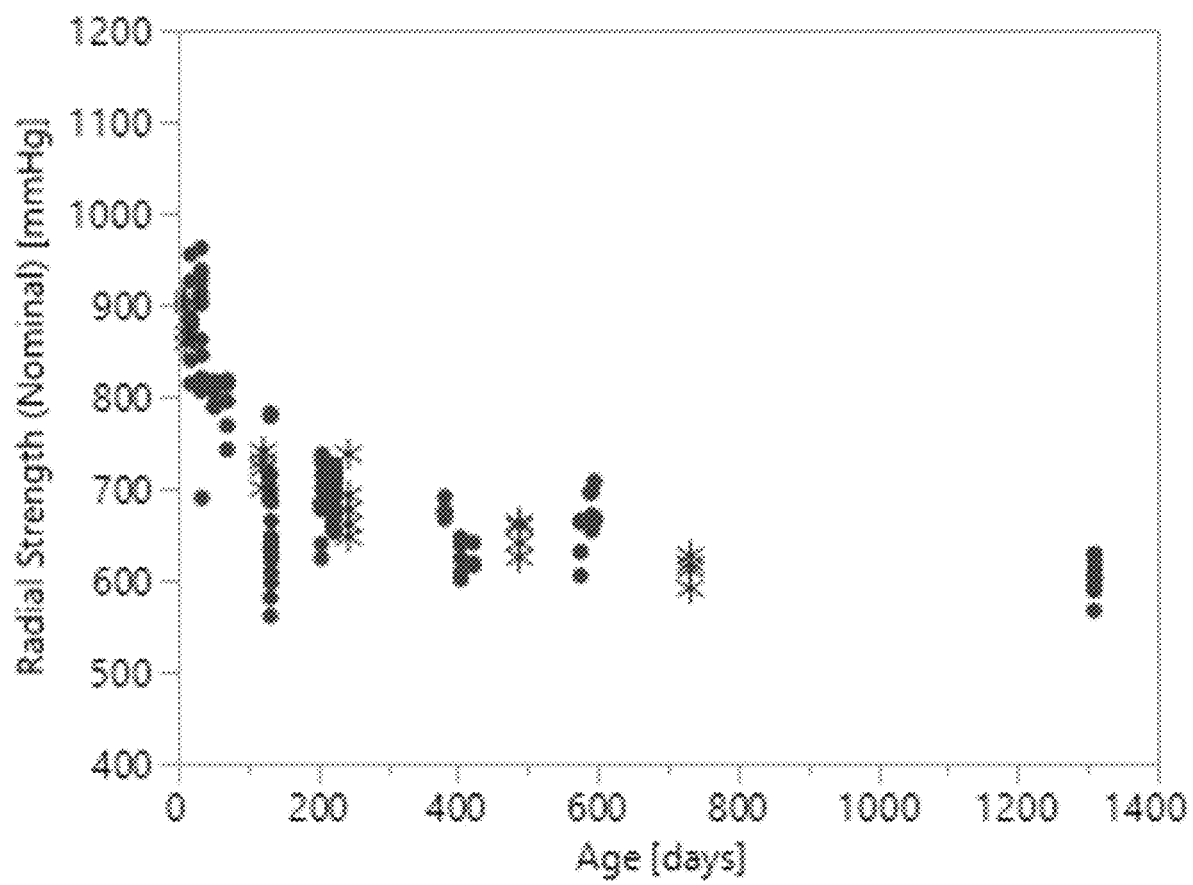
FIG. 6: depicts comparison of real-time aging data with water-accelerated aging conditions for nominal radial strength.

Table 2 and FIGS. 5 and 6 are the results for radial strength for nominal deployment. FIG. 5 depicts results for nominal radial strength of 3.0 mm diameter Absorb as a function of hours of water exposure time. FIG. 6: depicts comparison of real-time aging data (circles) with water-accelerated aging conditions (asterisks) for nominal radial strength of Absorb.

TABLE 2

Water-accelerated aging effect on nominal radial strength of Absorb.

| | Absorb GT1 BVS | |
|---|---|---|
| Time Point | Radial Strength (mmHg) | Stdev (mmHg) |
| Control (0 hrs) | 887 | 22 |
| 4 hours | 724 | 15 |
| 8 hours | 683 | 35 |
| 16 hours | 646 | 15 |
| 24 hours | 613 | 13 |

Figure 7:
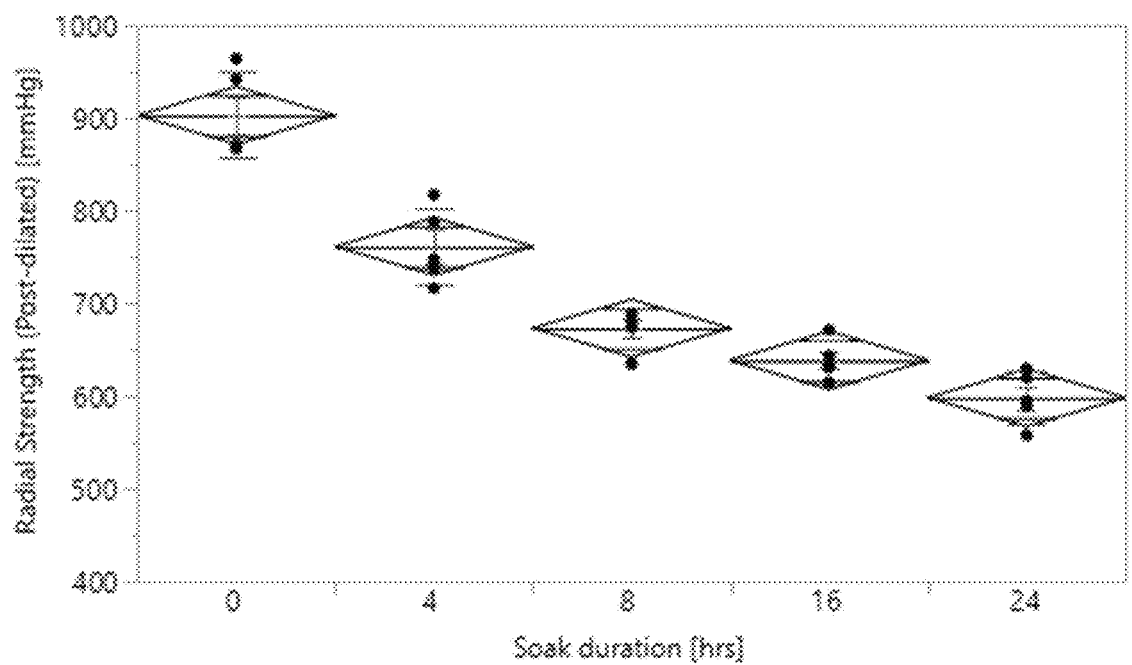
FIG. 7 depicts results for post-dilated radial strength of 3.0 mm diameter Absorb as a function of hours of water exposure time.
Figure 8:
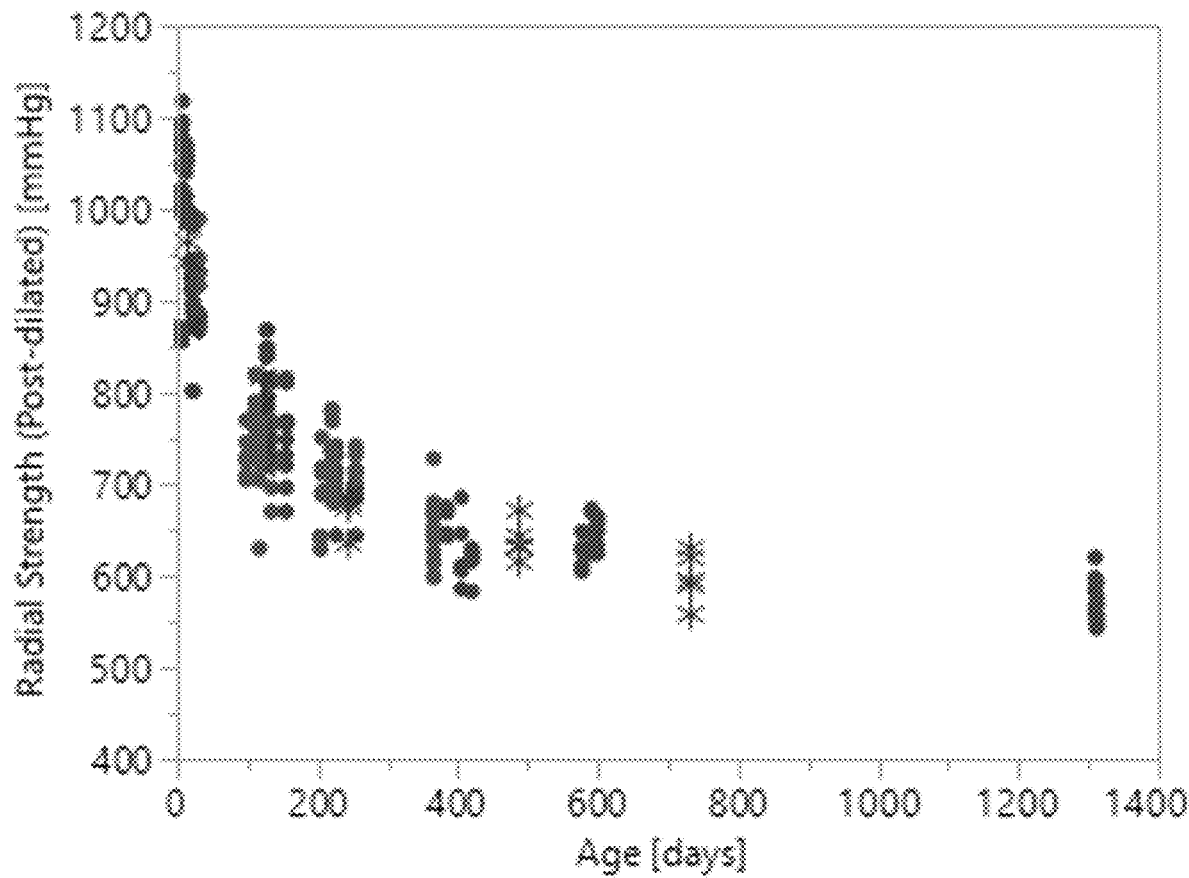
FIG. 8 depicts comparison of real-time aging data with water-accelerated aging conditions for post-dilated radial strength of Absorb.

Table 3 and FIGS. 7 and 8 are the results of radial strength for nominal deployment. FIG. 7 depicts results for post-dilated radial strength of 3.0 mm diameter Absorb as a function of hours of water exposure time. FIG. 8 depicts comparison of real-time aging data (circles) with water-accelerated aging conditions (asterisks) for post-dilated radial strength of Absorb.

TABLE 3

Water-accelerated aging effect on post-dilated radial strength of Absorb.

| | Absorb GT1 BVS | |
|---|---|---|
| Time Point | Radial Strength (mmHg) | Stdev (mmHg) |
| Control (0 hrs) | 903 | 47 |
| 4 hours | 761 | 41 |
| 8 hours | 673 | 22 |
| 16 hours | 639 | 21 |
| 24 hours | 599 | 28 |

Figure 9:
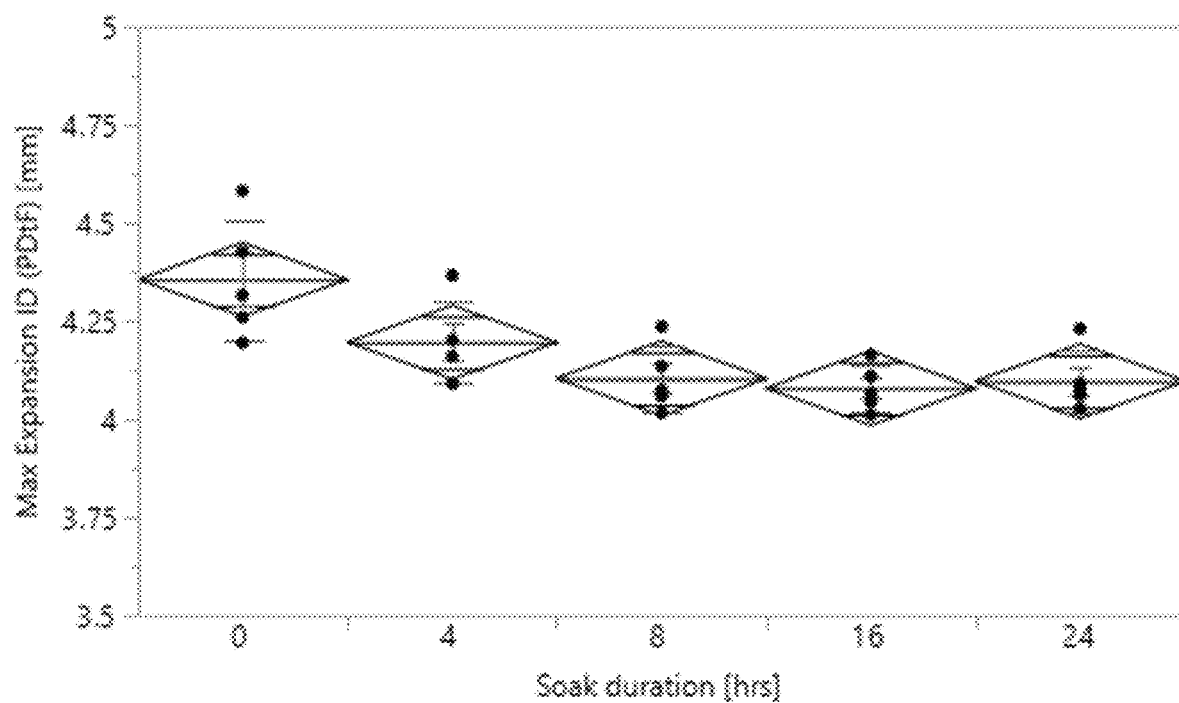
FIG. 9 depicts results for the Max Expansion ID (Post-Dilate to Fracture) data of 3.0 mm diameter Absorb as a function of water exposure time.
Figure 10:
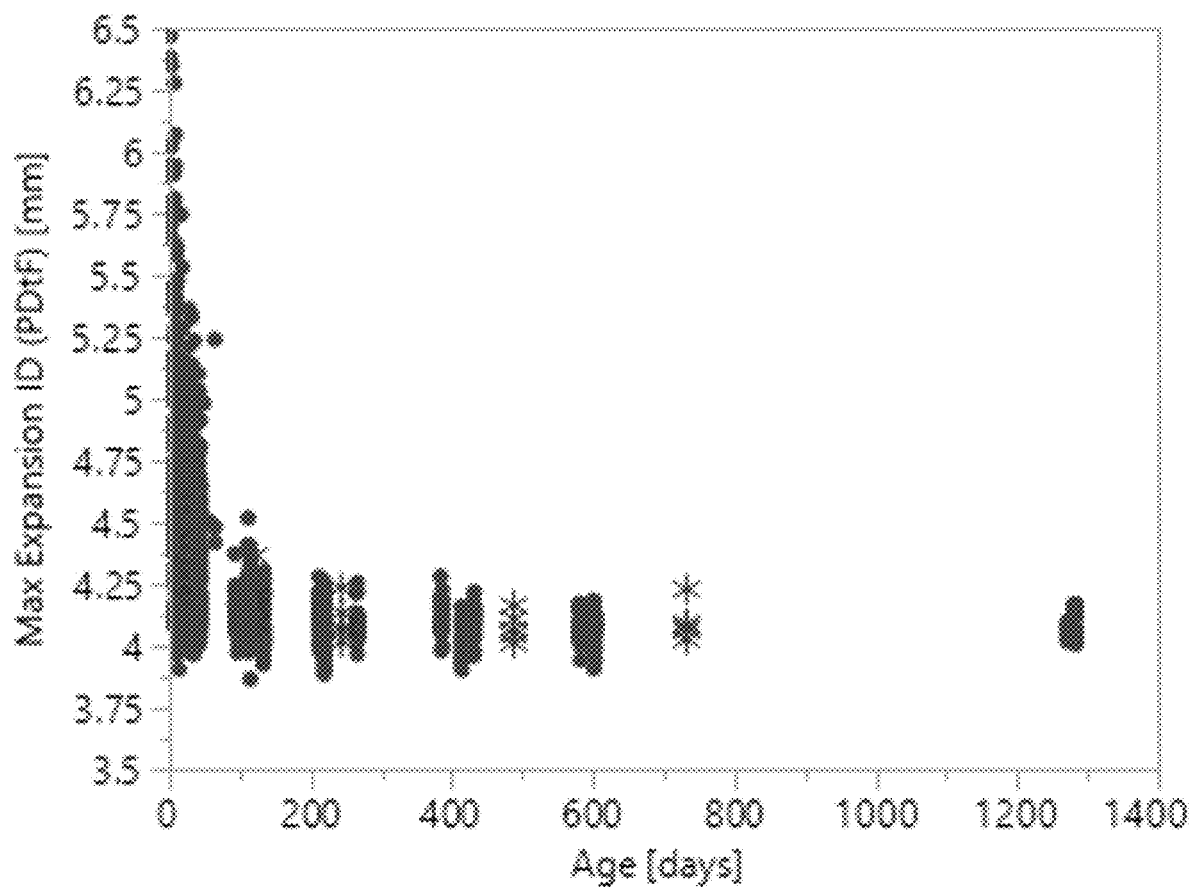
FIG. 10 depicts comparison of real-time aging data with water-accelerated aging conditions for Max Expansion ID (Post-Dilate to Fracture) of Absorb.

Table 4 and FIGS. 9 and 10 are the results for Post-Dilate to Fracture (PDtF). FIG. 9 depicts results for the Max Expansion ID (Post-Dilate to Fracture) data of 3.0 mm diameter Absorb as a function of water exposure time. FIG. 10 depicts comparison of real-time aging data (circles) with water-accelerated aging conditions (asterisks) for Max Expansion ID (Post-Dilate to Fracture) of 3.0 mm diameter Absorb.

TABLE 4

Water-accelerated aging effect on Max Expansion ID (Post-Dilate to Fracture) of Absorb.

| | Absorb GT1 BVS | |
|---|---|---|
| Time Point | Max Expansion ID (mm) | Stdev (mm) |
| Control (0 hrs) | 4.36 | 0.15 |
| 4 hours | 4.20 | 0.10 |
| 8 hours | 4.10 | 0.08 |
| 16 hours | 4.08 | 0.06 |
| 24 hours | 4.10 | 0.08 |

Figure 11:
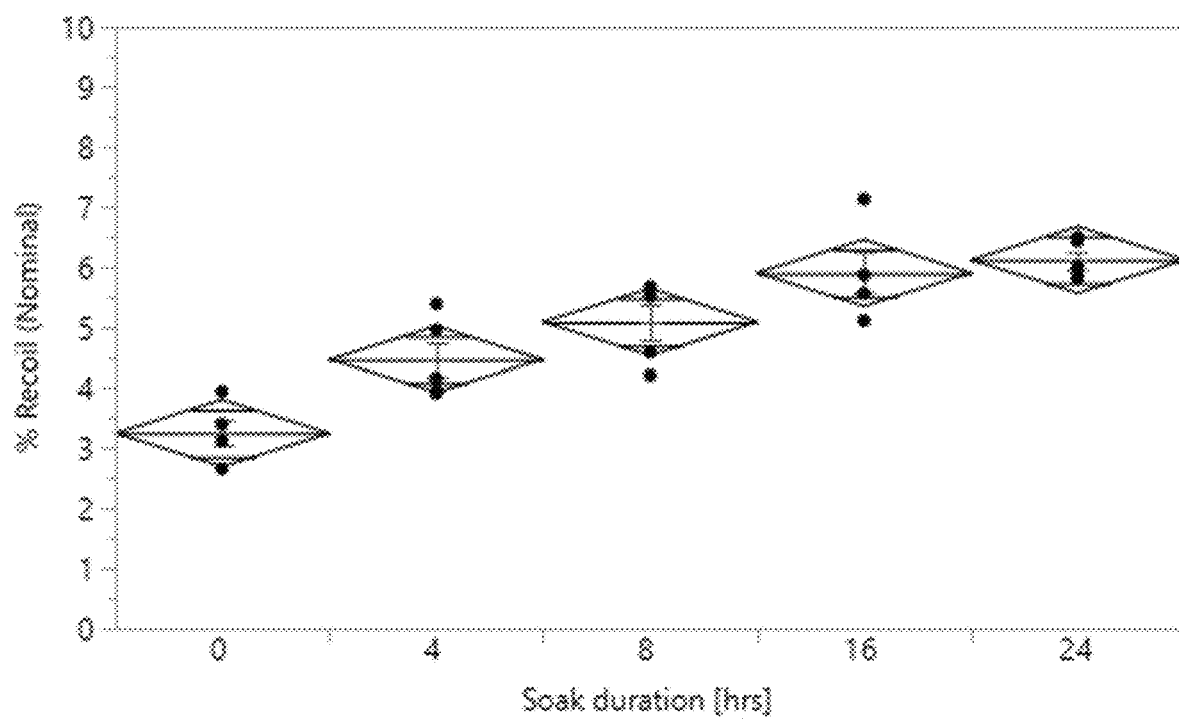
FIG. 11 depicts the % Recoil (Nominal) of 3.0 mm diameter Absorb as a function of water exposure time.
Figure 12:
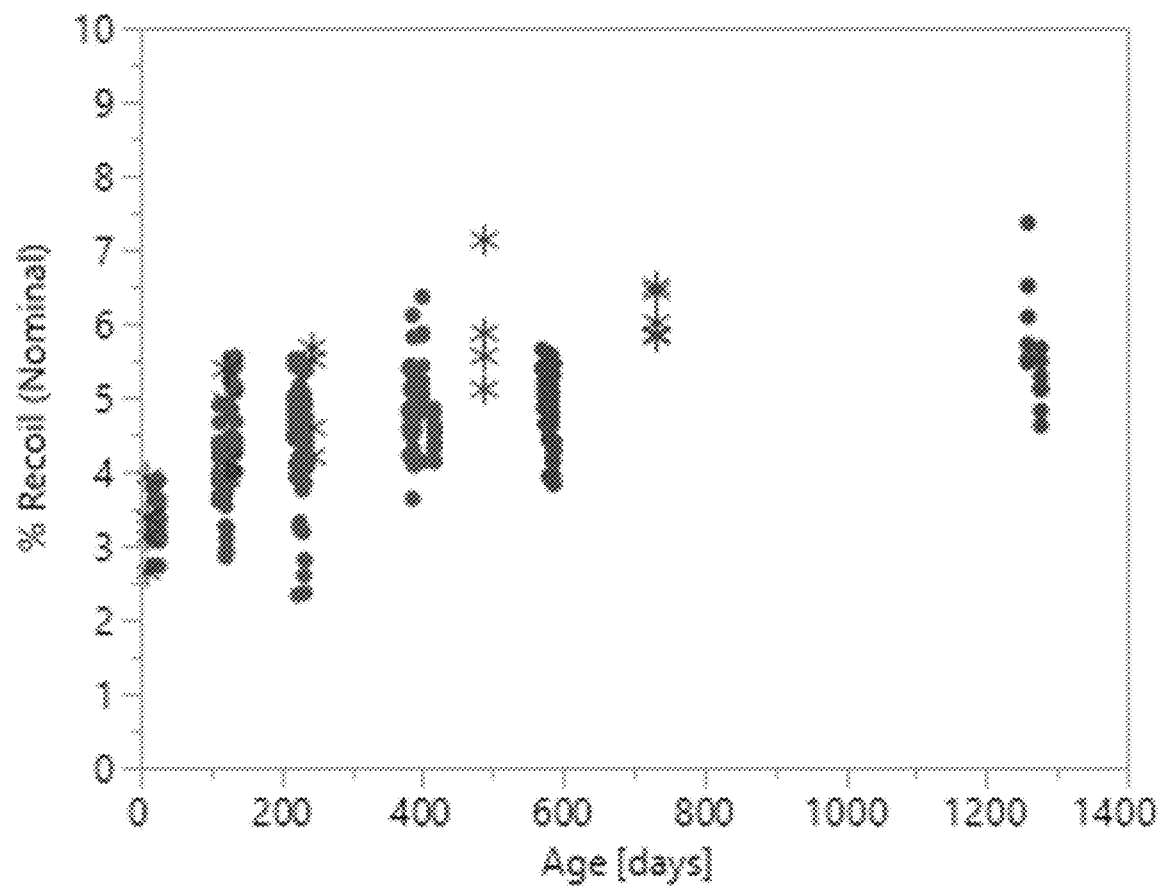
FIG. 12 depicts a comparison of real-time aging data with water-accelerated aging conditions for % Recoil of Absorb.

Table 5 and FIGS. 11 and 12 depict results for % Recoil at nominal deployment. FIG. 11 depicts the % Recoil (Nominal) of 3.0 mm diameter Absorb as a function of water exposure time. FIG. 12 depicts a comparison of real-time aging data (circles) with water-accelerated aging conditions (asterisks) for % Recoil (Nominal) of 3.0 mm diameter Absorb.

TABLE 5

Water Accelerated Aging Effect on % Recoil (Nominal) of Absorb.

| | Absorb GT1 BVS | |
|---|---|---|
| Time Point | Recoil (%) | Stdev (%) |
| Control (0 hrs) | 3.24 | 0.47 |
| 4 hours | 4.47 | 0.67 |
| 8 hours | 5.09 | 0.65 |
| 16 hours | 5.91 | 0.75 |
| 24 hours | 6.12 | 0.32 |

Figure 13:
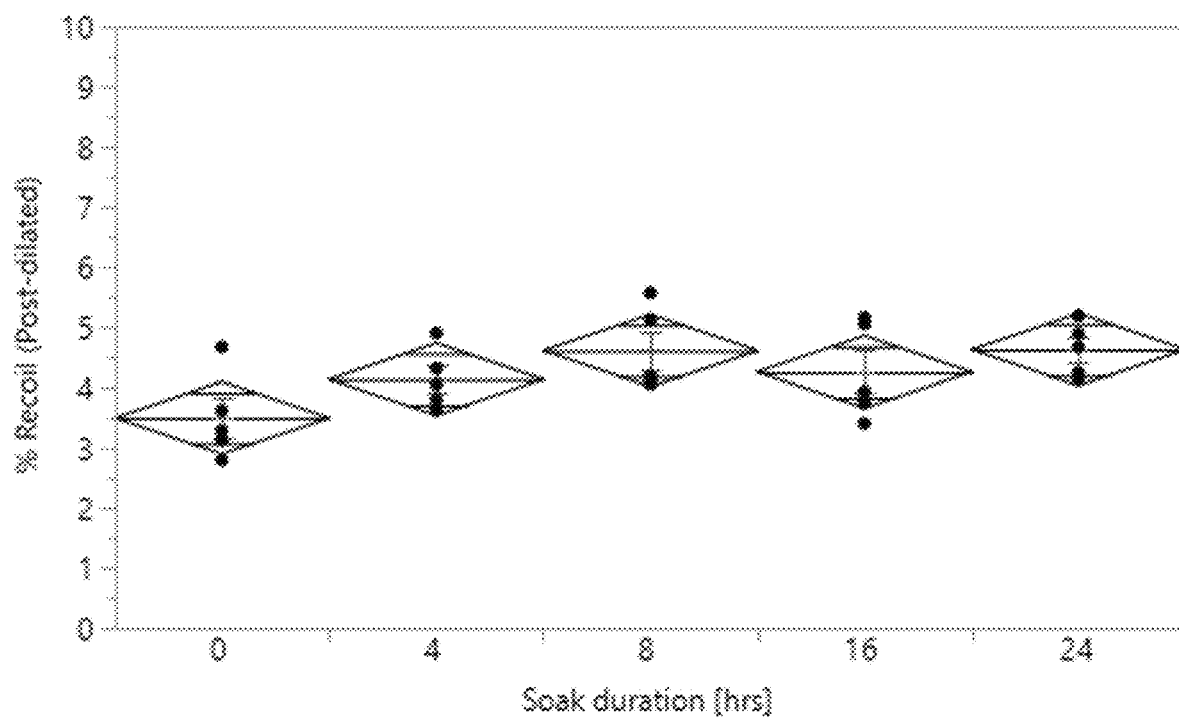
FIG. 13 depicts the % Recoil (post-dilated) of Absorb as a function of water exposure time.
Figure 14:
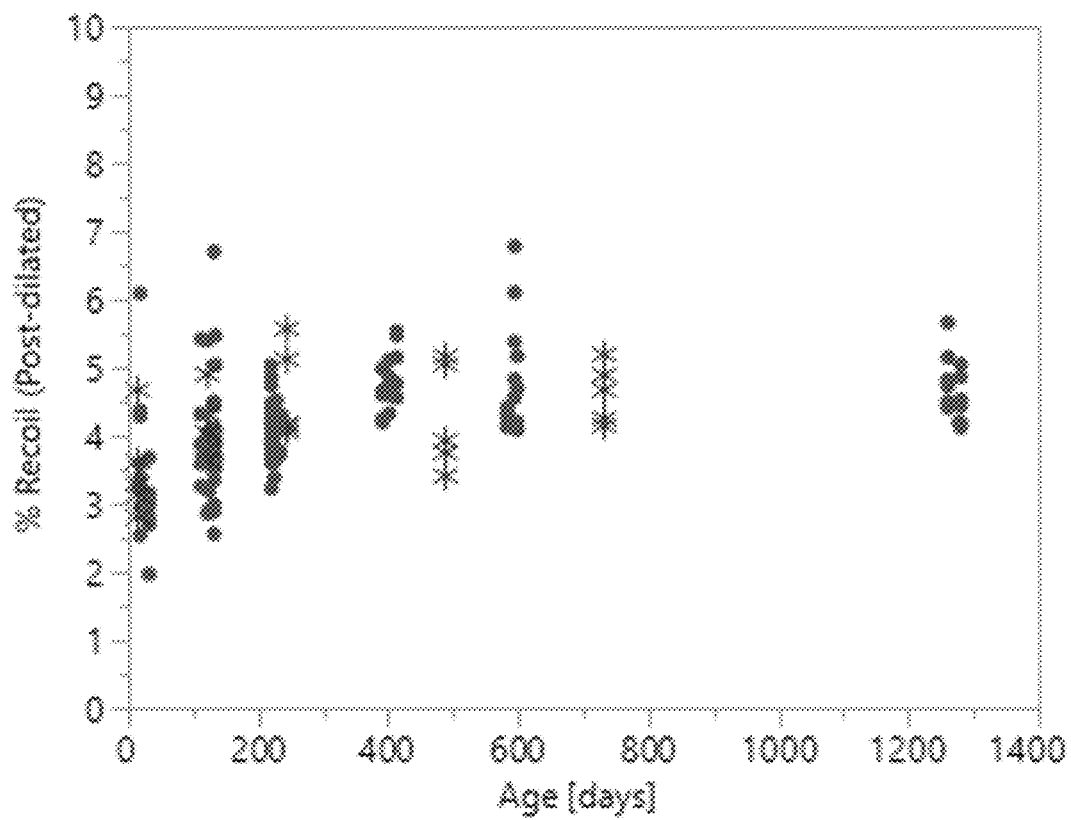
FIG. 14 depicts a comparison of real-time aging data with water-accelerated aging conditions for % Recoil (post-dilated) of Absorb.

Table 6 and FIGS. 13 and 14 depict results for % Recoil at post-dilated deployment. FIG. 13 depicts the % Recoil (post-dilated) of Absorb as a function of water exposure time. FIG. 14 depicts a comparison of real-time aging data (circles) with water-accelerated aging conditions (asterisks) for % Recoil (post-dilated) of Absorb.

TABLE 6

Water Accelerated Aging Effect on % Recoil (Post-dilated) of Absorb.

| | Absorb GT1 BVS | |
|---|---|---|
| Time Point | Recoil | Stdev |
| Control (0 hrs) | 3.50 | 0.72 |
| 4 hours | 4.14 | 0.50 |
| 8 hours | 4.61 | 0.69 |
| 16 hours | 4.26 | 0.79 |
| 24 hours | 4.63 | 0.44 |

Real-time data was collected beyond the shelf-life of Absorb, using samples over 3 years old which were manufactured using current commercial manufacturing processes, as well as out to 18 months. Data included in the comparison are a compilation of multiple lots to incorporate lot-to-lot variability. The accelerated water data overlaid at estimated "equivalent" time points show that all five outputs show reasonable correlation with the real-time data, or are worst-case relative to real-time.

Accelerated aging data has been placed on the real-time aging curves empirically, with each hour of soak time corresponding with a time interval of 30.5 days (one month) which represented the best convergence of accelerated data with real-time data. The 24 hour soak data has therefore been placed at 732 days, with the 4, 8 and 16 hour time points placed at 122 days (4 months), 244 days (8 months), and 488 days (16 months), respectively.

In all five functional outputs, the data for accelerated aging for 3.0 mm diameter Absorb after 24 hours of water exposure showed comparable performance relative to the longest available real-time aging time point, which was taken at approximately 3½ years after e-beam sterilization, well beyond the shelf life. Assigning each hour of soak duration to be equivalent to one month of real-time aging creates accelerated aging curves that follow the real-time aging behavior very closely, reinforcing the statement that 24 hours of soak duration can be compared to 24 months of real-time aging. This corresponds to an AAF of 732 (732 days/1 day).

This experimental evidence strengthens the rationale for using water exposure as an acceleration tool for aging of a PLLA scaffolds or PLLA-based scaffolds and as a surrogate for real-time aging for those critical functional outputs most affected by physical aging of the polymer substrate or backbone. This conclusion holds true across all sizes (manufactured diameters and balloon sizes) of Absorb, given the similarities in aging behavior observed.

Measurement of Tg using Dynamic Mechanical Analysis for the PLLA scaffolds submerged in water shows that the mechanical Tg decreases. This confirms that water plasticizes the PLLA molecules and hence increases the local chain mobility (fluidity). The increase of the chain mobility will further enable packing efficiency and chain rearrangement leading to an additional increase of Tg and increase of modulus (embrittlement). Measurement of Tg using DSC for Absorb samples after various durations of water soaking also demonstrates a Tg increase. Measurement of functional outputs demonstrates the similarity of the aging behavior of Absorb between real-time and water-accelerated aging, showing that the use of water-accelerated aging is an adequate surrogate for real-time aging. Therefore, both the theoretical and experimental results support the use of water accelerated aging to evaluate the performance of the Absorb and other PLLA-based products at their shelf life.

For example, for scaffold made from a blend of PLLA and poly(L-lactide-co-glycolide) random copolymer, the water accelerated aging conditions have been verified to 12 months. The PLLA composition is greater than 95 wt %. This allows developmental work to achieve the equivalent of 24 months of real-time aging in a 24 hour period.

Since the material composition for the PLLA blend is slightly different from a pure PLLA scaffold, it is expected that the ideal soak conditions may also change to reflect the difference in glass transition temperature of the scaffold substrate. This is consistent with the theory of the WLF equation, which shows how a material property can be shifted by temperature exposure. The difference between the applied temperature and the glass transition temperature impacts the magnitude of the shift. By depressing the glass transition temperature, the shift at a given applied temperature is greater. Water plasticizes the scaffold substrate, depressing the Tg for both the PLLA blend and pure PLLA. However, with the lower Tg of the blend, to get the same shift in properties, a lower temperature can be applied.

A robust body of data for any material proving water accelerated concept may be used for developmental work as well as potentially for regulatory submissions, improving time to market.

The polymer for a polymer carrier of a therapeutic coating over the scaffold may include poly(L-lactide) (PLLA), poly (DL-lactide) (PDLLA), polyglycolide, poly(L-lactide-co-glycolide), polycaprolactone, or poly(L-lactide-co-caprolactone). A drug may be mixed or dispersed throughout the polymer carrier. The drug may be 20 to 80 wt % of the therapeutic layer, or more narrowly, 30 to 70 wt %, 40 to 60 wt %, 45 to 55 wt %, or 50% of the therapeutic layer. The polymer may further include blends with or copolymers of polylactide and polydioxanone, polyethylene oxide, polyethylene glycol, poly(butylene succinate), poly(trimethylene carbonate), poly(butylene succinate), or any combination thereof.

The drug may include an antiproliferative, anti-inflammatory or immune modulating, anti-migratory, anti-thrombotic or other pro-healing agent or a combination thereof. The anti-proliferative agent can be a natural proteineous agent such as a cytotoxin or a synthetic molecule or other substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin I1, actinomycin X1, and actinomycin C1), all taxoids such as taxols, docetaxel, and paclitaxel, paclitaxel derivatives, all olimus drugs such as macrolide antibiotics, rapamycin, everolimus, novolimus, myolimus, deforolimus, umirolimus, biolimus, merilimus, temsirolimus structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives include 40-O-(3-hydroxy)propyl-rapamycin, 40-O-[2-(2-hydroxy)ethoxy] ethyl-rapamycin, or 40-O-tetrazole-rapamycin, 40-epi-(N1-tetrazolyl)-rapamycin (ABT-578 manufactured by Abbott Laboratories, Abbott Park, Ill.), prodrugs thereof, co-drugs thereof, and combinations thereof.

"Nominal" or "nominal diameter" may refer to the labeled inflation diameter of a balloon, e.g., a balloon labeled as "3.0 mm" has a nominal diameter or nominal inflation diameter of 3.0 mm which is the outer diameter of the balloon. "Post-dilated" or post-dilation balloon diameter may refer to inflation beyond the nominal balloon diameter, e.g., a 6.5 mm balloon has about a 7.4 mm post-dilation diameter, or a 6.0 mm ball. The nominal to post dilation ratios for a balloon may range from 1.05 to 1.15 (i.e., a post-dilation diameter may be 5% to 15% greater than a nominal inflated balloon diameter). The scaffold diameter, after attaining an inflated diameter by balloon pressure, will to some degree decrease in diameter due to recoil effects related primarily to, any or all of, the manner in which the scaffold was fabricated and processed, the scaffold material and the scaffold design.

The "glass transition temperature," Tg, is the temperature at which the amorphous domains of a polymer change from a brittle vitreous, glassy state to a solid deformable, rubbery or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is increased, the heat capacity increases. The increasing heat capacity corresponds to an increase in heat dissipation through movement. Tg of a given polymer can be dependent on the heating rate and can be influenced by the thermal history of the polymer as well as its degree of crystallinity. Furthermore, the chemical structure of the polymer heavily influences the glass transition by affecting mobility.

The Tg can be determined as the approximate midpoint of a temperature range over which the glass transition takes place. [ASTM D883-90]. The most frequently used definition of Tg uses the energy release on heating in differential scanning calorimetry (DSC). As used herein, the Tg refers to a glass transition temperature as measured by differential scanning calorimetry (DSC) at a 20° C./min heating rate. Unless stated otherwise, values for "Tg" refer to an upper limit for Tg (E.g., for poly(L-lactide) and the Tg when the material is dry. Poly(L-lactide) has a glass transition temperature range of between about 55 to 60 Deg. C "Tg" for poly(L-lactide), for purposes of this disclosure, Tg is 60 Deg. C), or up to 65 Deg. C for a strain hardened tube. The glass transition temperature is a function of chain flexibility. The glass transition occurs when there is enough vibrational (thermal) energy in the system to create sufficient free-volume to permit sequences of 6-10 main-chain carbons to move together as a unit. At this point, the mechanical behavior of the polymer changes from rigid and brittle to tough and leathery.

The Tg may also be determined by a mechanical method called Dynamics Mechanical Analysis (DMA). The Tg was determined by DMA according to ASTM E1640-13 using a tubular sample geometry DMA is a technique where a small deformation is applied to a sample in a cyclic manner. This allows the materials response to stress, temperature, frequency and other values to be studied. DMA works by applying a sinusoidal deformation to a sample of known geometry. The sample can be subjected by a controlled stress or a controlled strain. For a known stress, the sample will then deform a certain amount. In DMA this is done sinusoidally. DMA measures stiffness and damping, these are reported as modulus and tan delta. Because a sinusoidal force is applied, the modulus is expressed as an in-phase component, the storage modulus, and an out of phase component, the loss modulus. The storage modulus, E', is the measure of the sample's elastic behavior. The ratio of the loss to the storage is the tan delta and is often called damping and is a measure of the energy dissipation of a material.

The glass transition (Tg) is seen as a large drop (a decade or more) in the storage modulus when viewed on a log scale against a linear temperature scale. A concurrent peak in the tan delta is also seen. The value reported as the Tg varies with industry with the onset of the E' drop, the peak of the tan delta, and the peak of the E' curve being the most commonly used. E' Onset occurs at the lowest temperature and relates to mechanical failure. E Peak occurs at the middle temperature and is more closely related to the physical property changes attributed to the glass transition in plastics. It reflects molecular processes and agrees with the idea of Tg as the temperature at the onset of segmental motion. Tan Delta Peak occurs at the highest temperature.

The "melting temperature" (Tm) is the temperature at which a material changes from solid to liquid state. In polymers, Tm is the peak temperature at which a semicrystalline phase melts into an amorphous state. Such a melting process usually takes place within a relative narrow range (<20° C.), thus it is acceptable to report Tm as a single value.

"Modulus" may be defined as the ratio of a component of stress or force per unit area applied to a material divided by the strain along an axis of applied force that result from the applied force. For example, a material has both a tensile and a compressive modulus.

"Toughness", or "fracture toughness" is the amount of energy absorbed prior to fracture, or equivalently, the amount of work required to fracture a material. One measure of toughness is the area under a stress-strain curve from zero strain to the strain at fracture. The stress is proportional to the tensile force on the material and the strain is proportional to its length. The area under the curve then is proportional to the integral of the force over the distance the polymer stretches before breaking. This integral is the work (energy) required to break the sample. The toughness is a measure of the energy a sample can absorb before it breaks. There is a difference between toughness and strength. A material that is strong, but not tough is said to be brittle. Brittle materials are strong, but cannot deform very much before breaking.

The "degree of crystallinity" may be expressed in terms of, $w_c$ (mass fraction), $\varphi_c$ (volume fraction) and refers to mass fraction or volume fraction of crystalline phase in a sample of polymer. The mass-fraction and the volume-fraction degrees of crystallinity are related by the equation, $w_c = \varphi_c \rho / \rho_c$, where $\rho$ and $\rho_c$ are the mass concentrations (mass densities) of the entire sample and of the crystalline phase, respectively. The degree of crystallinity can be determined by several experimental techniques. Among the most commonly used are: (i) x-ray diffraction, (ii) calorimetry (DSC), (iii) mass density measurements, (iv) infrared spectroscopy (IR), (v) solid-state NMR spectroscopy, and (vi) vapor permeability. Unless stated otherwise, throughout this description a degree of crystallinity given for a polymer is expressed as a percentage (%) of crystallinity and expressed as a mass or volume fraction. Unless stated otherwise throughout this description a degree of crystallinity given for a polymer composition is expressed as a percentage (%) of crystallinity and expressed as a mass fraction. Measurements of crystallinity may also be determined from a modified method of differential scanning calorimetry (DSC), e.g., over a temperature range of 0 Deg. C to 200 Deg. C, with modulation amplitude of 0.5° C. and heat rate of 6° C./minute and duration of 1 minute.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

What is claimed is:

1. A method of accelerated aging of a bioresorbable polymeric scaffold comprising:
    providing a bioresorbable polymeric scaffold having a structure composed of a network of interconnecting struts, wherein scaffold is in a crimped configuration;
    exposing the scaffold to water at a controlled temperature for a selected aging time less than a desired shelf life of the scaffold, wherein a functional output of the scaffold changes during the exposing; and
    measuring the functional output of the scaffold;
    wherein the selected aging time and the controlled temperature are such that the functional output measured is within 10% of a measured functional output of the scaffold from real time aging 100 to 1000 times longer than the selected aging time.

2. The method of claim 1, wherein the functional output is radial strength which is decreased by the accelerated aging.

3. The method of claim 1, wherein the functional output is expandability which is decreased by the accelerated aging.

4. The method of claim 1, wherein the functional output is recoil post-deployment.

* * * * *